(12) United States Patent
Baba et al.

(10) Patent No.: US 11,701,195 B2
(45) Date of Patent: Jul. 18, 2023

(54) OPTICAL FILM, CONNECTING MEMBER, ENDOSCOPE CAMERA DRAPE, ENDOSCOPE DEVICE, MEDICAL SYSTEM, OPTICAL FILM PRODUCTION METHOD, AND CONNECTING MEMBER PRODUCTION METHOD

(71) Applicant: DEXERIALS CORPORATION, Tokyo (JP)

(72) Inventors: Yukihisa Baba, Tokyo (JP); Masanori Takeuchi, Tokyo (JP)

(73) Assignee: DEXERIALS CORPORATION, Tokyo (JP)

( * ) Notice: Subject to any disclaimer, the term of this patent is extended or adjusted under 35 U.S.C. 154(b) by 822 days.

(21) Appl. No.: 15/760,688

(22) PCT Filed: Oct. 13, 2016

(86) PCT No.: PCT/JP2016/080382
§ 371 (c)(1),
(2) Date: Mar. 16, 2018

(87) PCT Pub. No.: WO2017/065217
PCT Pub. Date: Apr. 20, 2017

(65) Prior Publication Data
US 2018/0256274 A1    Sep. 13, 2018

(30) Foreign Application Priority Data

Oct. 14, 2015 (JP) ................................. 2015-202793
Oct. 13, 2016 (JP) ................................. 2016-201425

(51) Int. Cl.
*A61B 46/10* (2016.01)
*G02B 1/118* (2015.01)
(Continued)

(52) U.S. Cl.
CPC ............ *A61B 46/10* (2016.02); *A61B 1/0011* (2013.01); *A61B 1/00105* (2013.01);
(Continued)

(58) Field of Classification Search
CPC .............. A61B 1/00105; A61B 1/0011; A61B 1/00126; A61B 1/00142; A61B 1/00186;
(Continued)

(56) References Cited

U.S. PATENT DOCUMENTS 5,792,045 A * 8/1998 Adair ................. A61B 1/00128
600/125
6,019,719 A    2/2000 Schulz et al.
(Continued)

FOREIGN PATENT DOCUMENTS

CN    101042442 A    9/2007
CN    103048705 A    4/2013
(Continued)

OTHER PUBLICATIONS

Apr. 13, 2020, Chinese Office Action issued for related CN Application No. 201680060130.1.
(Continued)

*Primary Examiner* — Aaron B Fairchild
*Assistant Examiner* — Stephen Floyd London
(74) *Attorney, Agent, or Firm* — Paratus Law Group, PLLC (57) ABSTRACT

There is provided a new and improved optical film, connecting member, endoscope camera drape, endoscope device, medical system, optical film production method, and connecting member production method capable of suppressing quality degradation of a captured image while also protecting the endoscope camera from airborne droplets, the optical film provided on the endoscope camera drape including: a drape section that covers a circumferential face of an (Continued)

endoscope camera, and a connecting member which is provided on a front end of the drape section and connects an endoscope and the endoscope camera, the optical film being provided on the connecting member, and including: a reflection suppression section configured to suppress a reflection of incident light incident on the endoscope camera from the endoscope.

15 Claims, 6 Drawing Sheets

(51) Int. Cl.
    *A61B 1/00*     (2006.01)
    *A61B 1/04*     (2006.01)
    *A61B 1/07*     (2006.01)
    *G02B 23/24*     (2006.01)
    *G02B 23/26*     (2006.01)
    *G02B 1/111*     (2015.01)

(52) U.S. Cl.
    CPC ...... *A61B 1/00126* (2013.01); *A61B 1/00142* (2013.01); *A61B 1/042* (2013.01); *A61B 1/07* (2013.01); *G02B 1/111* (2013.01); *G02B 1/118* (2013.01); *G02B 23/2469* (2013.01); *G02B 23/26* (2013.01)

(58) Field of Classification Search
    CPC ........... A61B 1/042; A61B 1/07; A61B 1/127; A61B 1/253; A61B 46/10; A61B 1/00096; G02B 1/111; G02B 1/118; G02B 3/0056; G02B 5/285; G02B 5/287; G02B 23/2469; G02B 23/26; G02B 1/115
    See application file for complete search history.

(56) References Cited

U.S. PATENT DOCUMENTS

| | | | |
|---|---|---|---|
| 6,123,080 A | 9/2000 | Mohan et al. | |
| 2005/0182321 A1* | 8/2005 | Frangioni | A61B 1/043 600/431 |
| 2010/0033819 A1* | 2/2010 | Schulz | G02B 1/14 359/507 |
| 2011/0051249 A1* | 3/2011 | Endoh | G02B 1/118 359/599 |
| 2014/0098422 A1* | 4/2014 | Fukuda | B29D 11/00346 359/601 |
| 2014/0177059 A1 | 6/2014 | Ishimatsu et al. | |
| 2014/0233104 A1* | 8/2014 | Nagahama | G02B 5/0231 359/585 |
| 2015/0037535 A1* | 2/2015 | Akimoto | C09C 1/3072 428/141 |
| 2016/0061996 A1* | 3/2016 | Ishimatsu | G02B 1/113 359/586 |
| 2017/0108627 A1* | 4/2017 | Chou | G02B 13/0045 |
| 2017/0123110 A1* | 5/2017 | Nakamatsu | G02B 27/0006 |

FOREIGN PATENT DOCUMENTS

| | | | | |
|---|---|---|---|---|
| CN | 103518149 A | | 1/2014 | |
| EP | 0573158 A1 | | 12/1993 | |
| EP | 2923630 A1 | | 9/2015 | |
| EP | 3162274 A1 | | 5/2017 | |
| GB | 2483154 A | | 2/2012 | |
| GB | 2483154 B | * | 7/2015 | ............. A61B 46/10 |
| JP | S60-95418 A | | 5/1985 | |
| JP | H07-204211 | | 8/1995 | |
| JP | H08-206056 A | | 8/1996 | |
| JP | 2002-267815 A | | 9/2002 | |
| JP | 2005-031538 A | | 2/2005 | |
| JP | 2005-208519 A | | 8/2005 | |
| JP | 2006-043128 A | | 2/2006 | |
| JP | 2010-220683 A | | 10/2010 | |
| JP | 2014-113243 A | | 6/2014 | |
| WO | WO-2014112555 A1 | * | 7/2014 | ............. G02B 1/118 |

OTHER PUBLICATIONS

Oct. 15, 2020, Chinese Office Action issued for related CN Application No. 201680060130.1.
Oct. 16, 2020, Taiwanese Office Action issued for related TW Application No. 105133196.
Sep. 23, 2020, Japanese Office Action issued for related JP application No. 2016-201425.
Aug. 5, 2019, Chinese Office Action issued for related CN Application No. 201680060130.1.
Apr. 25, 2019, European Search Report issued for related EP application No. 16855470.7.
Feb. 26, 2020, Taiwanese Office Action issued for related TW Application No. 105133196.
Mar. 16, 2022, European Communication issued for related EP Application No. 16855470.7.

* cited by examiner

OPTICAL FILM, CONNECTING MEMBER, ENDOSCOPE CAMERA DRAPE, ENDOSCOPE DEVICE, MEDICAL SYSTEM, OPTICAL FILM PRODUCTION METHOD, AND CONNECTING MEMBER PRODUCTION METHOD

CROSS REFERENCE TO PRIOR APPLICATION

This application is a National Stage Patent Application of PCT International Patent Application No. PCT/JP2016/080382 (filed on Oct. 13, 2016) under 35 U.S.C. §371, which claims priority to Japanese Patent Application Nos. 2015-202793 (filed on Oct. 14, 2015) and 2016-201425 (filed on Oct. 13, 2016), which are all hereby incorporated by reference in their entirety.

TECHNICAL FIELD

The present invention relates to an optical film, a connecting member, an endoscope camera drape, an endoscope device, a medical system, an optical film production method, and a connecting member production method.

BACKGROUND ART

Recently, as disclosed in Patent Literatures 1 to 5, for example, technology that covers an endoscope camera and an endoscope camera cable with an endoscope camera drape has been proposed. According to this technology, even if the endoscope camera and the endoscope camera cable are not sterilized, the dispersal of bacteria and the like adhering to the surface of the endoscope camera and the endoscope camera cable inside the operating room can be suppressed. Also, the contamination of the endoscope camera and the endoscope camera cable by airborne droplets such as bodily fluids can be suppressed. For this reason, since the replacement frequency of the endoscope camera and the endoscope camera cable during surgery is reduced, a shortening of surgery time, a reduction of the physical burden on the patient, and the like can be expected. Also, since a sterilization process of the endoscope camera and the endoscope camera cable becomes unnecessary, advantageous effects such as a reduction of surgical costs and an improvement in the life of the endoscope camera and the endoscope camera cable can also be expected.

In the technology disclosed in Patent Literature 1, a grip is provided on a front end of a drape section. Additionally, in this technology, a through hole is provided in the front end of the grip, and an insertion section of an endoscope (that is, the part which is fed into the body of a patient) is passed through the through hole. Additionally, the grip covers a connecting part between the endoscope and an endoscope camera. The practitioner operates the endoscope primarily by holding the grip. In the technologies disclosed in Patent Literatures 2 to 4, the front end of a drape section is attached to a base section of an endoscope (that is, the part attached to an endoscope camera). In the technology disclosed in Patent Literature 5, a connecting member is provided on the front end of the drape section. The connecting member blocks the opening of the front end of the drape section. Also, the connecting member connects the endoscope and the endoscope camera. Also, a central part of the connecting member (that is, the part through which incident light incident on the endoscope camera from the endoscope passes) is configured with a transparent member.

CITATION LIST

Patent Literature

Patent Literature 1: JP H8-206056A
Patent Literature 2: JP 2014-113243A
Patent Literature 3: JP 2006-43128A
Patent Literature 4: JP 2010-220683A
Patent Literature 5: GB 2483154B

SUMMARY OF INVENTION

Technical Problem

However, in the technology disclosed in Patent Literature 1, there is a problem in that it is extremely difficult to maintain airtightness between the wall surface of the through hole and the insertion section of the endoscope. For this reason, in the technology disclosed in Patent Literature 1, there is a problem of the possibility that airborne droplets may intrude into the drape section from a gap between the wall surface of the through hole and the insertion section of the endoscope. Also, in Patent Literatures 2 to 4, there is a problem in that it is difficult to maintain airtightness between the front end of the drape section and the endoscope. For this reason, in the technologies disclosed in Patent Literatures 2 to 4, there is a problem of the possibility that airborne droplets may intrude into the drape section from a gap between the front end of the drape section and the endoscope. Also, in the technologies disclosed in Patent Literatures 1 to 4, in the case of detaching the endoscope from the endoscope camera covered by the drape section, it is necessary to either detach the endoscope, including the drape section, from the endoscope camera, or detach the endoscope from the drape section and the endoscope camera. In the former case, the endoscope camera is exposed. Even in the latter case, since the front end of the drape section has an opening, the endoscope camera is exposed from the opening. For this reason, the work of attaching and detaching the endoscope from the endoscope camera must be performed in a place where there is no concern of contamination by airborne droplets.

On the other hand, in the technology disclosed in Patent Literature 5, the endoscope camera is covered by the connecting member and the drape section. Furthermore, since the endoscope is attachable and detachable from the connecting member, the endoscope can be attached and detached from the endoscope camera in a state in which the endoscope camera is covered by the connecting member and the drape section. Consequently, the above problem is less likely to occur. However, in the technology disclosed in Patent Literature 5, since the central part of the connecting member is simply configured with a transparent member, there is a possibility that incident light may reflect at this part. If incident light reflects at the connecting member, there is a possibility of degraded quality of a captured image taken by the endoscope camera.

Accordingly, the present invention has been devised in light of the above problems, and an objective of the present invention is to provide a new and improved optical film, connecting member, endoscope camera drape, endoscope device, medical system, optical film production method, and connecting member production method capable of suppressing quality degradation of a captured image while also protecting the endoscope camera from airborne droplets.

Solution to Problem

To solve the above problem, according to an aspect of the present invention, there is provided an optical film provided on an endoscope camera drape including a drape section that covers a circumferential face of an endoscope camera, and a connecting member which is provided on a front end of the drape section and connects an endoscope and the endoscope camera, the optical film being provided on the connecting member, and including: a reflection suppression section configured to suppress a reflection of incident light incident on the endoscope camera from the endoscope.

Here, the reflection suppression section may be a concave-convex structure formed on a surface of the optical film, and an average cycle of concavities and convexities included in the concave-convex structure may be less than or equal to a visible light wavelength.

In addition, a spectral reflectance of visible light may be from 0.1% to 1.8%.

In addition, the reflection suppression section may suppress fogging of the optical film.

In addition, the reflection suppression section may include a hydrophilic resin.

In addition, a polycarbonate resin may be included.

In addition, the optical film may include a substrate film, and the reflection suppression section formed on a surface of the substrate film, and the substrate film may include the polycarbonate resin.

According to another aspect of the present invention, there is also provided a connecting member including: the optical film. The connecting member is provided on a front end of a drape section that covers a circumferential face of an endoscope camera, and connects an endoscope and the endoscope camera.

Here, the connecting member may include the optical film.

In addition, a protective film that covers the optical film may be included.

In addition, the protective film may be a molded item having a shape conforming to a surface shape of the connecting member.

According to another aspect of the present invention, there is provided an endoscope camera drape including: a drape section that covers a circumferential face of an endoscope camera; and the connecting member.

According to another aspect of the present invention, there is provided an endoscope device including: the endoscope camera drape.

According to another aspect of the present invention, there is provided a medical system including: the endoscope device.

According to another aspect of the present invention, there is provided an optical film production method for producing an optical film provided on an endoscope camera drape including a drape section that covers a circumferential face of an endoscope camera, and a connecting member which is provided on a front end of the drape section and connects an endoscope and the endoscope camera, the optical film being provided on the connecting member, the optical film production method including: a first step of preparing a substrate film; and a second step of forming, on a surface of the substrate film, a reflection suppression section that suppresses a reflection of incident light incident on the endoscope camera from the endoscope.

Here, in the second step, a concave-convex structure may be formed on the surface of the optical film as the reflection suppression section, and an average cycle of concavities and convexities included in the concave-convex structure may be less than or equal to a visible light wavelength.

In addition, the reflection suppression section may include a hydrophilic resin.

In addition, the substrate film may include a polycarbonate resin.

According to another aspect of the present invention, there is provided a connecting member production method of producing a connecting member provided on a front end of a drape section that covers a circumferential face of an endoscope camera, the connecting member connecting an endoscope and the endoscope camera, the connecting member production method including: manufacturing the connecting member using the optical film.

Here, the connecting member may be manufactured by monolithically molding the optical film in a shape of the connecting member.

ADVANTAGEOUS EFFECTS OF INVENTION

According to the present invention as described above, the endoscope camera can be protected from airborne droplets by the connecting member and the drape section. Furthermore, the optical film provided on the connecting member is provided with a reflection suppression section that suppresses the reflection of incident light incident on the endoscope camera from the endoscope. Consequently, quality degradation of a captured image can be suppressed.

BRIEF DESCRIPTION OF DRAWINGS

[FIG. 1]

[FIG. 2]

[FIG. 3]

[FIG. 4]

[FIG. 5]

[FIG. 6]

[FIG. 7]

DESCRIPTION OF EMBODIMENTS

Hereinafter, (a) preferred embodiment(s) of the present invention will be described in detail with reference to the appended drawings. Note that, in this specification and the appended drawings, structural elements that have substantially the same function and structure are denoted with the same reference numerals, and repeated explanation of these structural elements is omitted.

<1. Overall Configuration of Endoscope Device>

Figure 1:
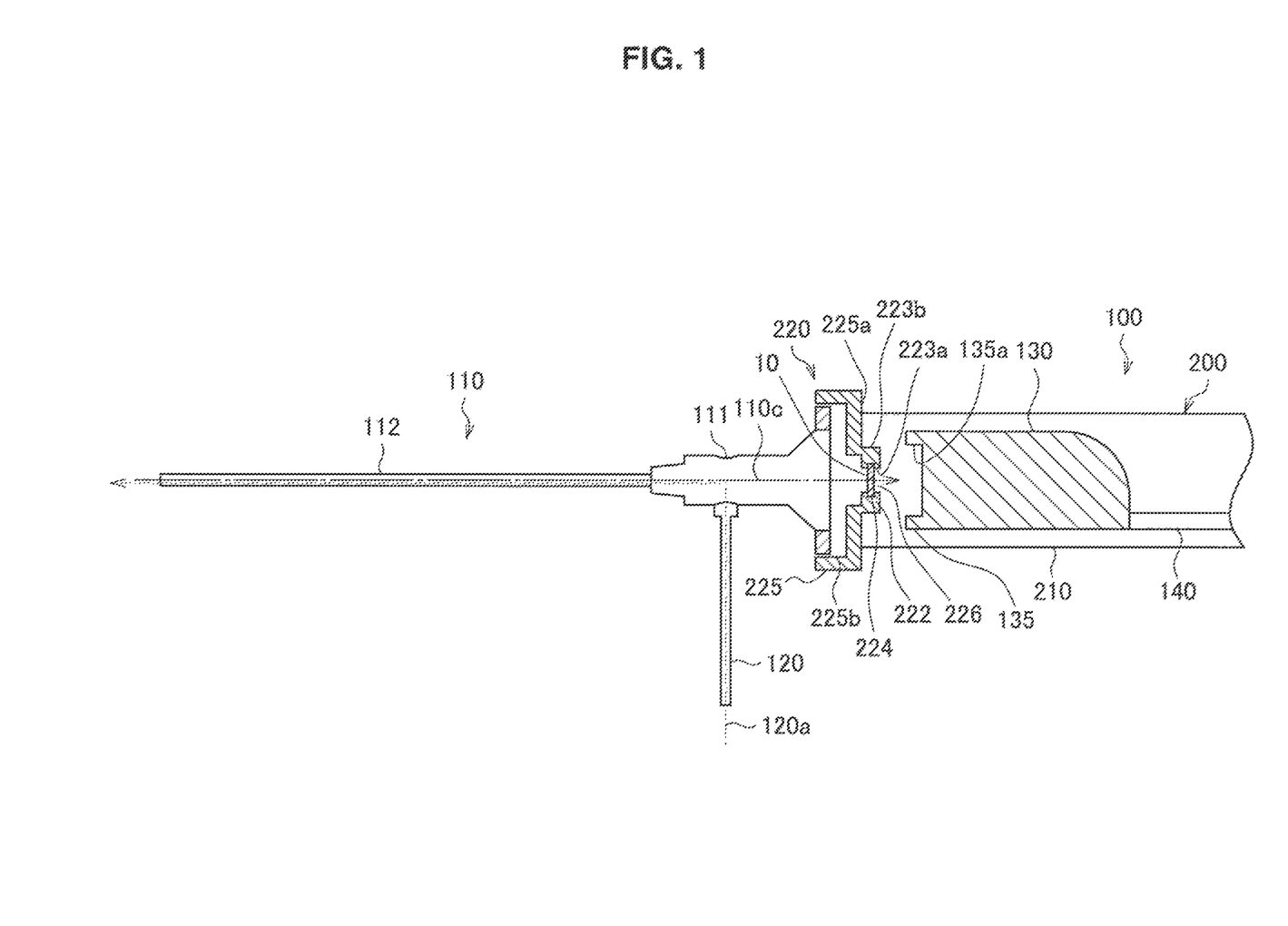
FIG. 1 is a sectional side view illustrating an exemplary configuration of an endoscope device according to an embodiment of the present invention.

First, an overall configuration of an endoscope device 100 according to the present embodiment will be described on the basis of FIG. 1. The endoscope device 100 is provided with an endoscope 110, a light radiation cable 120, an endoscope camera 130, an endoscope camera cable 140, and an endoscope camera drape 200.

The endoscope 110 is provided with a base section 111 and an insertion section 112. The light radiation cable 120 is connected to a side face of the base section 111, and the insertion section 112 is connected to a front end section of the base section 111. The base section 111 supplies the insertion section 112 with irradiating light supplied from the light radiation cable 120. Also, the base section 111 emits imaging light (that is, irradiating light reflected inside the body of a patient) supplied from the insertion section 112 to the endoscope camera 130 side. Note that an arrow 120a in FIG. 1 indicates the optical path of the irradiating light, while an arrow 110c indicates the optical path of the imaging light. Also, the rear end of the base section 111 is attachable and detachable from a connecting member 220 of the endoscope camera drape 200.

The insertion section 112 is the part inserted into the body of the patient. Irradiating light is emitted from the front end of the insertion section 112, and is reflected inside the body of the patient. Subsequently, the irradiating light reflected inside the body of the patient, or in other words, the imaging light is incident on the front end of the insertion section 112, passes through the interior of the insertion section 112, and reaches the base section 111. After that, the imaging light passes through the base section 111 and the connecting member 220, and is incident on the endoscope camera 130. The light radiation cable 120 supplies the interior of the endoscope 110 with light produced from a light source which is not illustrated. Note that the irradiating light is visible light, but may also be another type of light (for example, infrared light).

Note that the shape of the endoscope 110 is not particularly limited. For example, in FIG. 1, the insertion section 112 is a rigid insertion section, but may also be a flexible insertion section.

The endoscope camera 130 receives imaging light incident from the endoscope 110, and generates a captured image. The endoscope camera cable 140 transmits the captured image generated by the endoscope camera 130 to a display device or the like. The endoscope camera 130 and the endoscope camera cable 140 are not particularly limited, and a publicly known endoscope camera and endoscope camera cable can be applied arbitrarily.

Also, on the front end section of the endoscope camera 130, a concave connecting member engagement section 135 is provided. The connecting member engagement section 135 is attachable and detachable from an endoscope camera engagement section 222 of the connecting member 220.

The endoscope camera drape 200 is provided with a drape section 210 and the connecting member 220. The drape section 210 is a tubular and flexible member, and covers the circumferential surface of the endoscope camera 130 and the endoscope camera cable 140. The drape section 210 is subjected to a sterilization process. Also, the material of the drape section 210 is not particularly limited, and may include a material similar to that of a publicly known drape section. For example, the drape section 210 may include polyethylene or the like. Also, a housing section (a so-called container section) that houses the endoscope camera drape 200 may be connected to the rear end of the drape section 210.

On the front end of the drape section 210, the connecting member 220 is provided. The connecting member 220 blocks the opening of the front end of the drape section 210. The connecting member 220 is provided with the endoscope camera engagement section 222, an endoscope engagement section 225, and an optical film 10.

The endoscope camera engagement section 222 is a member that holds the optical film 10, and in addition, as described later, is attachable and detachable from the connecting member engagement section 135. Specifically, in a central part of the endoscope camera engagement section 222 (specifically, the part through which the imaging light passes), there is formed a through hole 226 that penetrates the endoscope camera engagement section 222 in the thickness direction. Note that the planar view shape of the through hole 226 (that is, the cross-sectional shape perpendicular to the thickness direction of the endoscope camera engagement section 222) may be circular, rectangular, or some other shape. Also, on a wall surface 223a of the through hole 226, a groove 224 is formed. The groove 224 is formed along the entire length in the circumferential direction of the wall surface 223a. Additionally, the optical film 10 is fitted into the groove 224. With this arrangement, the endoscope camera engagement section 222 holds the optical film 10. Note that the method by which the endoscope camera engagement section 222 holds the optical film 10 is not limited to this example. For example, the optical film 10 may also be weld-deposited onto the endoscope camera engagement section 222.

Also, the endoscope camera engagement section 222 is attachable and detachable from the connecting member engagement section 135. The structure for enabling the attachability and detachability of the connecting member engagement section 135 and the endoscope camera engagement section 222 is not particularly limited. For example, an engaging convexity may be formed on an outer circumferential surface 223b of the endoscope camera engagement section 222, and a groove that engages with the convexity may be formed on an inner circumferential surface 135a of the connecting member engagement section 135. Alternatively, screw ridges that thread into each other may be formed on the outer circumferential surface 223b of the endoscope camera engagement section 222 and the inner circumferential surface 135a of the connecting member engagement section 135. Also, the outer circumferential surface 223b of the endoscope camera engagement section 222 may be perpendicular to an outer circumferential base section 225a of the endoscope engagement section 225, but preferably is inclined slightly inward (that is, towards the center of the connecting member 220) on the connecting member engagement section 135 side. In this case, the attachment and detachment between the connecting member 220 and the endoscope camera 130 becomes easy. Note that the inclination angle of the outer circumferential surface 223b (that is, the angle between the outer circumferential surface 223b and the outer circumferential base section 225a of the endoscope engagement section 225) preferably is approximately from 80° to 90°, for example.

The endoscope engagement section 225 is provided on the surface of the endoscope camera engagement section 222 on the endoscope 110 side. The endoscope engagement section 225 is a concave member, and is attachable and detachable from the base section 111 of the endoscope 110. The structure for enabling the attachability and detachability of the endoscope engagement section 225 and the base section 111 is not particularly limited. For example, an engaging groove may be formed on an inner circumferential surface 225b of the endoscope engagement section 225, and a convexity that engages with the groove may be formed on the outer circumferential surface of the base section 111. Alternatively, screw ridges that thread into each other may be formed on the inner circumferential surface 225b of the endoscope engagement section 225 and the outer circumferential surface of the base section 111. Also, the drape section 210 is connected to the outer circumferential base section 225a of the endoscope engagement section 225.

The material included in the endoscope camera engagement section 222 and the endoscope engagement section 225 is not particularly limited, and may be a material similar to that of a publicly known connecting member. For example, the endoscope camera engagement section 222 and the endoscope engagement section 225 may also include polyethylene or the like, and obviously may include a material of the same type as that of the optical film 10.

The optical film 10 is held by the endoscope camera engagement section 222. Also, the optical film 10 is disposed in the central part of the connecting member 220, or in other words, on the optical path of the imaging light. Also, on both the front and back faces of the optical film 10, there is formed a reflection suppression section 12 described later. The reflection suppression section 12 suppresses the reflection of incident light (that is, imaging light) incident on the endoscope camera 130 from the endoscope 110. With this arrangement, the endoscope camera 130 is able to generate a clearer captured image. In other words, in the present embodiment, quality degradation of the captured image can be suppressed. Also, the drape section 210 and the connecting member 220 of the endoscope camera drape 200 are able to cover the endoscope camera 130 and the endoscope camera cable 140, regardless of the attached or detached state of the endoscope 110. Consequently, the endoscope camera drape 200 is able to protect the endoscope camera 130 and the endoscope camera cable 140 from airborne droplets, regardless of the attached or detached state of the endoscope 110.

Note that the configuration of the connecting member 220 is not limited to the configuration described above. In other words, the connecting member 220 may be of any type, insofar as the following characteristics are included.

(1) The opening on the front end of the drape section 210 is blocked.
(2) The endoscope 110 and the endoscope camera 130 are attachable and detachable.
(3) The optical film 10 is disposed on the optical path of the imaging light.

<2. Endoscope Camera Drape Production Method>

Next, a method for producing the endoscope camera drape 200 will be described. First, among the connecting member 220, the endoscope camera engagement section 222 and the endoscope engagement section 225 are manufactured by a publicly known formation method. On the other hand, the optical film 10 is manufactured by the production method described later. Next, by fitting the optical film 10 into the groove 224 of the endoscope camera engagement section 222, the connecting member 220 is manufactured. Next, the connecting member 220 and the front end of the drape section 210 are connected (for example, weld-deposited). By the above steps, the endoscope camera drape 200 is manufactured.

<3. Various Modifications>

(3-1. First Modification)

Figure 2:
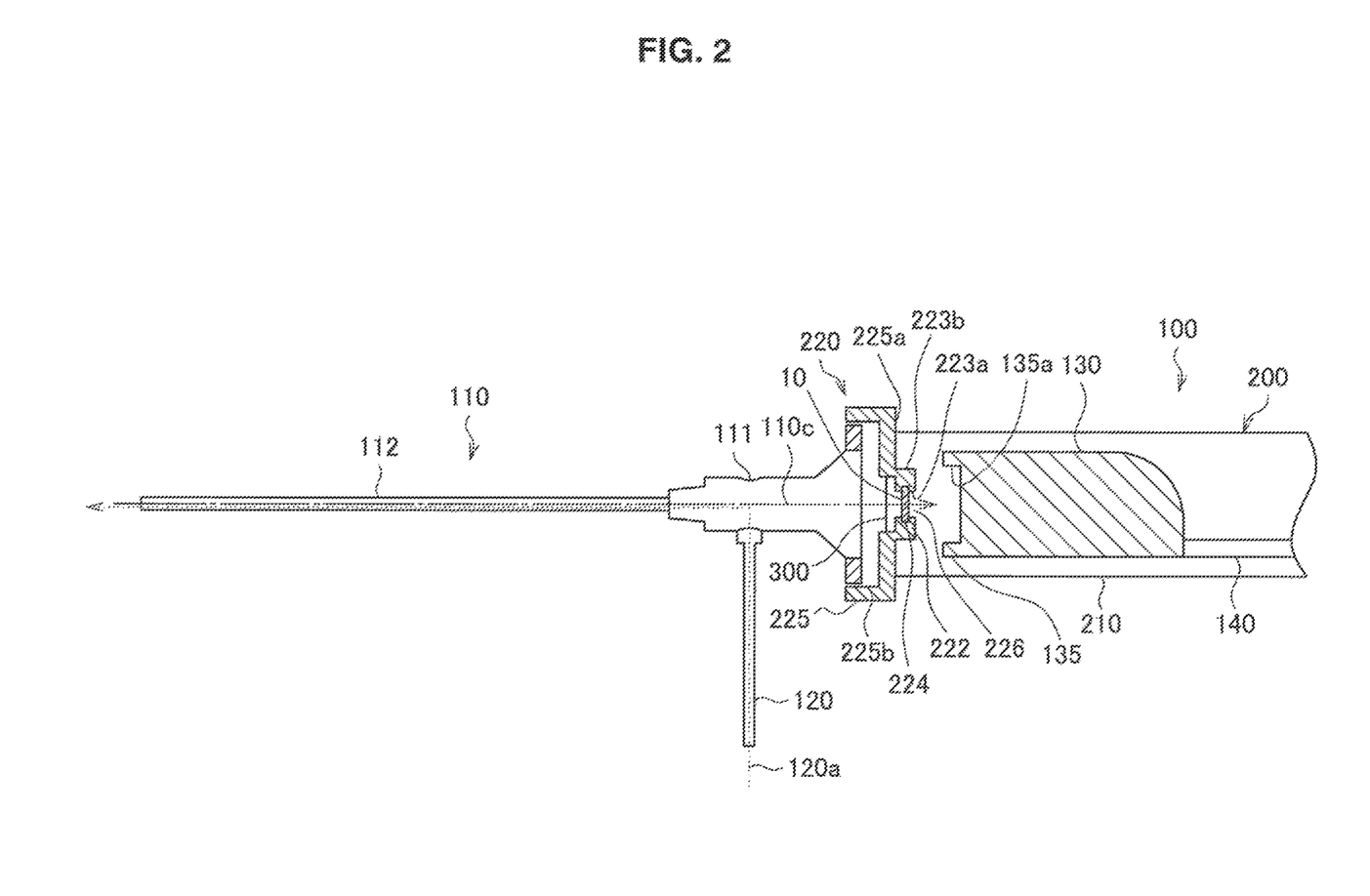
FIG. 2 is a sectional side view illustrating a first modification of an endoscope device.

Next, a first modification of the endoscope device 100 will be described on the basis of FIG. 2. In the first modification, the exposed face of the optical film 10 on the endoscope 110 side is covered by a protective film 300. With this arrangement, the optical film 10 can be protected from pollution and the like when the endoscope camera drape 200 is unused. Note that the optical film 10 has a fogging suppression function in some cases, but the protective film 300 is not necessarily required to have a fogging suppression function. Also, the protective film 300 preferably has a reflection suppression function equal to or greater than the optical film 10. Methods for raising the reflection suppression function of the protective film 300 include, for example, a method for providing a concave-convex structure on the protective film 300 and making the pitch of the concavities and convexities smaller than the pitch of the concavities and convexities of the reflection suppression section 12, and the like. In this case, the reflection suppression function of the optical film 10 is less likely to be impaired by the protective film 300. Consequently, even in the state in which the optical film 10 is covered by the protective film 300, the reflection suppression function of the optical film 10 can be evaluated more accurately. Consequently, the quality of the endoscope camera drape 200 (specifically, the reflection suppression function and the cleanliness) can be improved more consistently.

Additionally, the protective film 300 may also be colored. In this case, forgetting to remove the protective film 300 during use of the endoscope camera drape 200 can be prevented more reliably.

(3-2. Second Modification)

Figure 3:
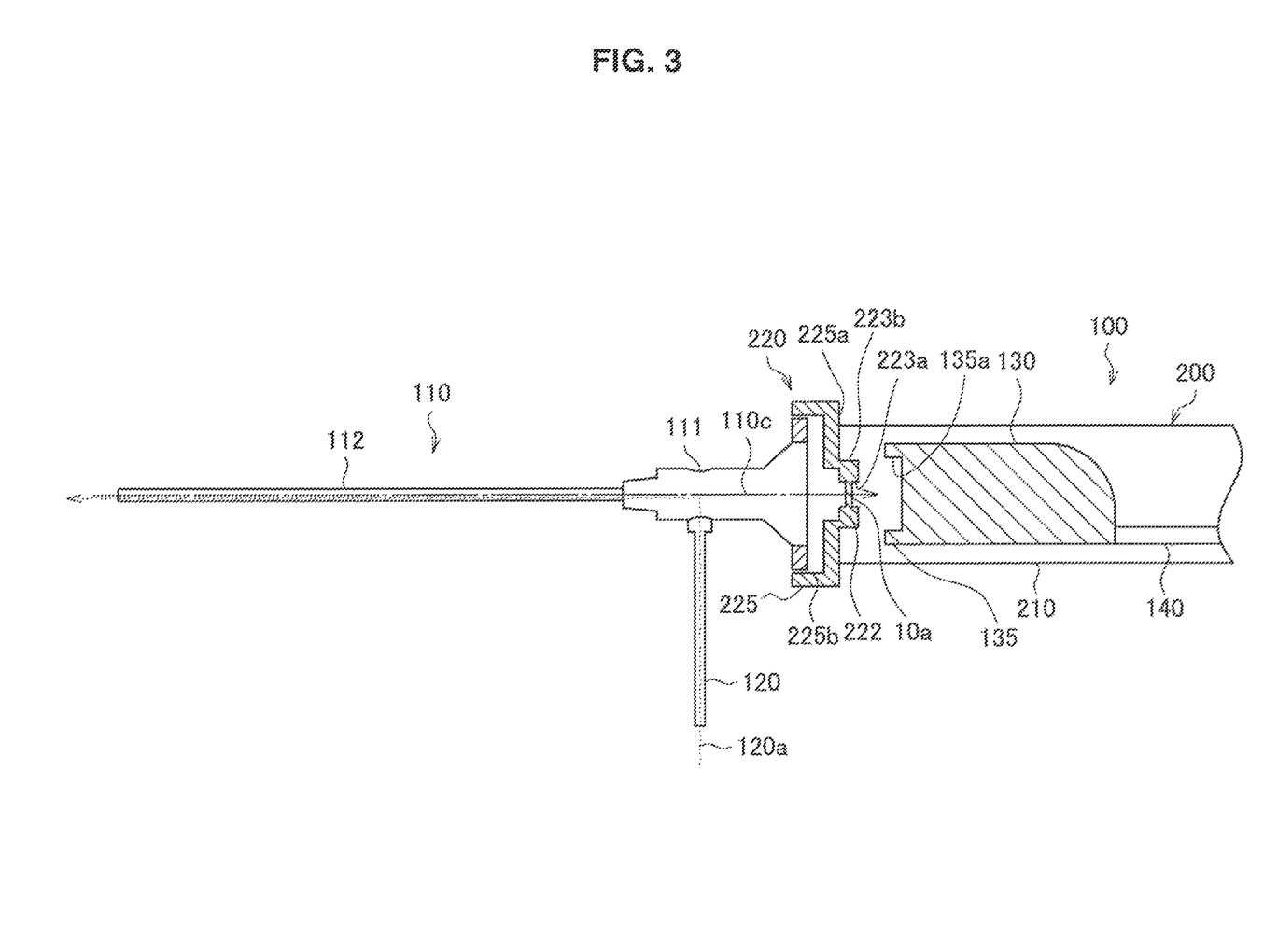
FIG. 3 is a sectional side view illustrating a second modification of an endoscope device.

Next, a second modification of the endoscope device 100 will be described on the basis of FIG. 3. In the second modification, the connecting member 220 is a monolithic molding of the optical film 10. Consequently, the connecting member 220 includes the optical film 10. In the second modification, imaging light passes through a central part 10a of the connecting member 220. In the second modification, the number of parts of the connecting member 220 can be decreased, and thus the production costs of the connecting member 220 can be decreased. Also, in the case of FIG. 1, there is a possibility of unsteadiness occurring between the optical film 10 and the groove 224. In addition, when such unsteadiness occurs, positional misalignment, inclination, and the like of the optical film 10 may occur. Furthermore, when positional misalignment, inclination, and the like of the optical film 10 occurs, there is a possibility of degraded quality of the captured image. On the other hand, in this second modification, positional misalignment, inclination, and the like of the optical film 10 are unlikely to occur, and thus the quality of the captured image can be improved further. Obviously, even in the case of FIG. 1, the quality of the captured image is improved as compared to the past. Also, in the second modification, the airtightness by the connecting member 220 can be raised further.

The method for monolithically molding the connecting member 220 is not particularly limited, but from the perspective of minimizing damage to the reflection suppression section 12, vacuum forming or pressure forming is preferable. Also, there is a possibility that the outer circumferential surface 223b of the endoscope camera engagement section 222 may ripple during vacuum forming or pressure forming. Accordingly, the endoscope camera engagement section 222 may be produced larger than the actual dimensions, and afterwards, the endoscope camera engagement section 222 may be trimmed.

(3-3. Third Modification)

Figure 4:
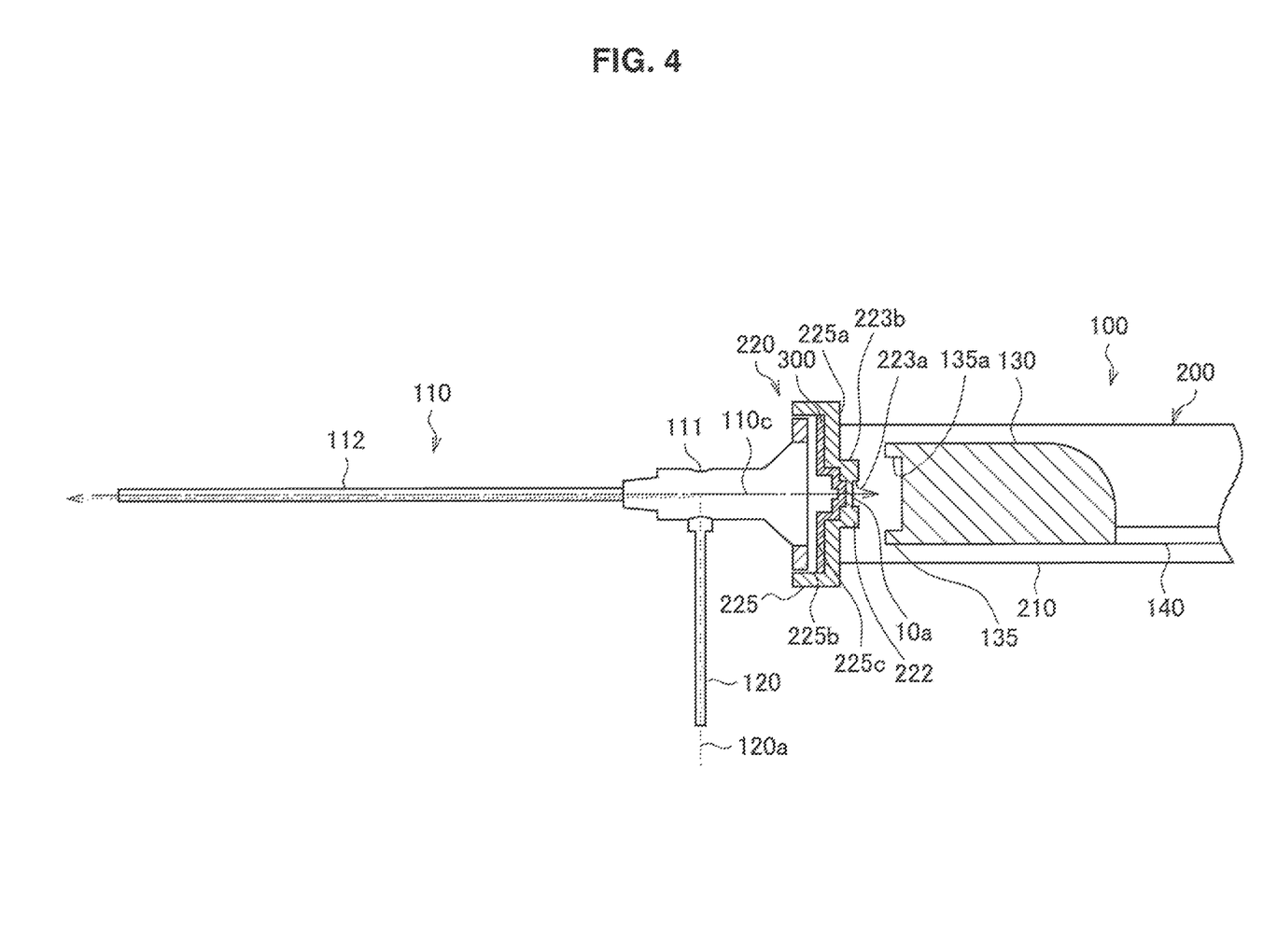
FIG. 4 is a sectional side view illustrating a third modification of an endoscope device.

Next, a third modification of the endoscope device 100 will be described on the basis of FIG. 4. In the third modification, the protective film 300 is a molded item having a shape conforming to the surface shape of the connecting member 220. Specifically, the protective film 300 has a shape conforming to an inner circumferential base face 225c of the endoscope engagement section 225, the surface of the endoscope camera engagement section 222 on the endoscope 110 side, and the surface of the central part 10a on the endoscope 110 side. The method for molding the protective film 300 is not particularly specified, and may be any conventional molding method. The functions included in the protective film 300 preferably are similar to those of the first modification. Note that, in FIG. 4, the connecting member 220 is a monolithically molded item according to the second modification. Obviously, the protective film 300 may also cover the connecting member 220 illustrated in FIG. 1. Also, the connecting member 220 according to the second modification may be covered by the protective film 300 according to the first modification.

(3-4. Fourth Modification)

Figure 5:
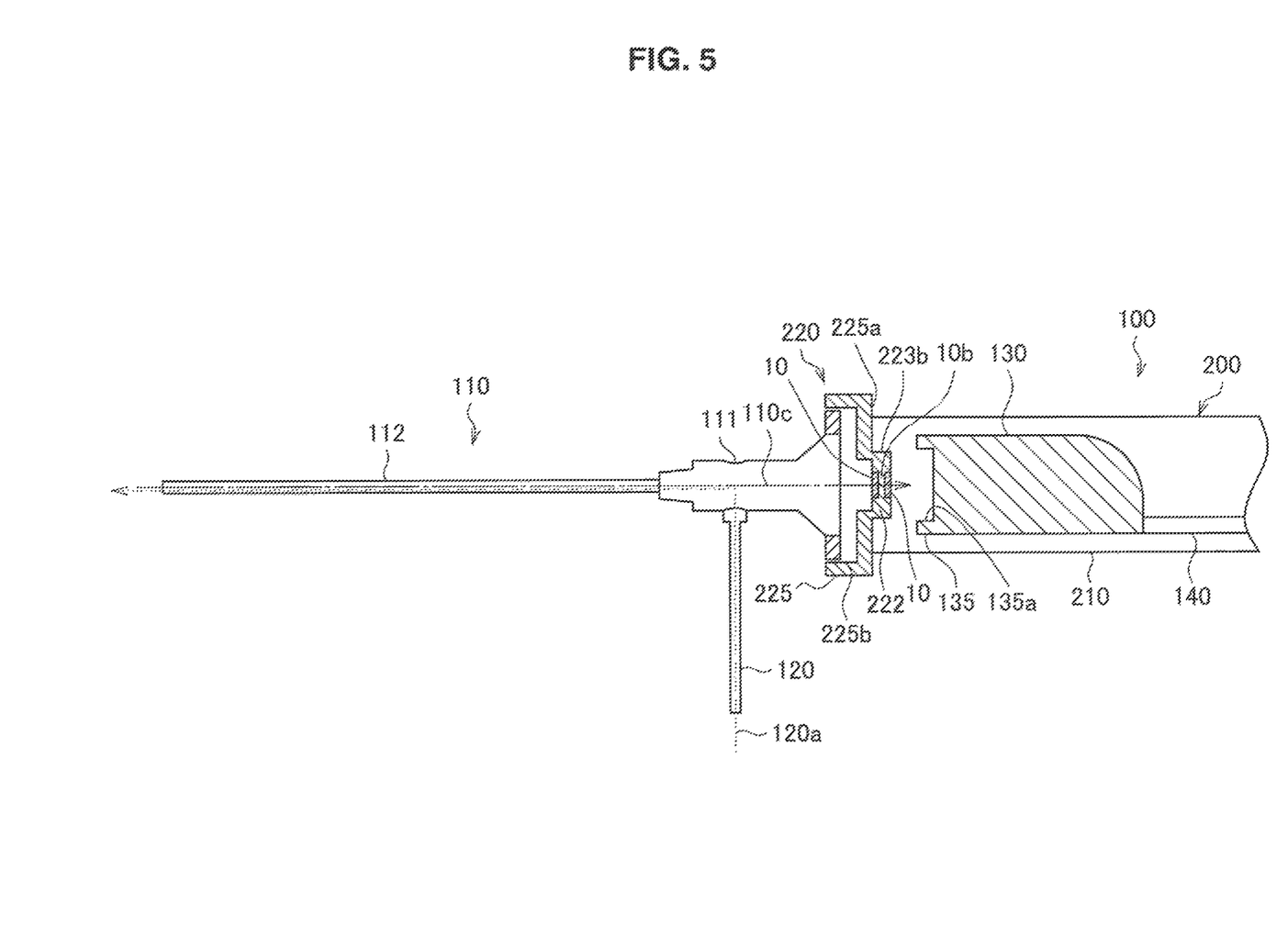
FIG. 5 is a sectional side view illustrating a fourth modification of an endoscope device.

Next, a fourth modification of the endoscope device 100 will be described on the basis of FIG. 5. In the fourth modification, the through hole 226 of the connecting member 220 is blocked by a blocking section 10b. Herein, the blocking section 10b is a monolithic molding of the endoscope camera engagement section 222 and the endoscope engagement section 225. Also, the connecting member 220 includes a transparent material. Herein, the transparent material may be the material included in an included substrate film 11. The method for monolithically molding the connecting member 220 may be similar to that of the second modification. Additionally, the optical film 10 is bonded to both the front and back faces of the blocking section 10b. The optical film 10 is bonded to the blocking section 10b with, for example, a transparent adhesive (such as double-sided tape, for example). Note that the optical film 10 may also be provided on only one of both the front and back faces of the blocking section 10b.

<4. Medical System>

The endoscope device 100 illustrated in FIGS. 1 to 5 can be applied to an arbitrary medical system. For example, the endoscope device 100 can be applied to a medical system provided with an operating table, a display device, and the like. In this case, the endoscope camera cable 140 is connected to the display device to use the endoscope device 100.

<5. Configuration of Optical Film>

Next, a detailed configuration of the optical film 10 will be described on the basis of FIGS. 6 and 7. As described above, the optical film 10 is a member that suppresses the reflection of imaging light. The optical film 10 is provided with the substrate film 11 and the reflection suppression section 12.

(5-1. Configuration of Substrate Film)

The substrate film 11 includes a material that is at least transparent. The material included in the substrate film 11 is not particularly limited insofar as the material is transparent. The material included in the substrate film 11 may be, for example, a plastic material or the like.

Herein, examples of the plastic material applicable to the substrate film 11 include methyl methacrylate (co-)polymers, polycarbonate, triacetyl cellulose, polyethylene, polyethylene terephthalate, polyethylene naphthalate, polystyrene, styrene (co-)polymers, methyl methacrylate-styrene copolymers, polymethyl methacrylate, cellulose diacetate, cellulose triacetate, cellulose acetate butyrate, polyvinyl alcohol, polyester, polyamide, polyimide, polyether sulfone, cycloolefin, polysulfone, polypropylene, polymethylpentene, polyvinyl chloride, polyvinyl acetal, polyether ketone, polyurethane, and glass. Among these, a particularly preferable material is polycarbonate. By having the substrate film 11 include polycarbonate, the transparency of the substrate film 11, and by extension the optical film 10, can be raised. In addition, polycarbonate is also a preferable material from the perspective of being easy to work, shock-resistant, and versatile.

In the case in which the substrate film 11 includes the above plastic material, the substrate film 11 is formed by a method such as by stretching the above plastic material, or by depositing in a film after diluting in a solvent, and then drying.

The thickness of the substrate film 11 is not particularly limited, and may be decided appropriately in accordance with the characteristics (for example, durability) demanded of the connecting member 220, or the like. Note that a "film" in the present embodiment is assumed to include a "sheet", a "plate", and the like.

(5-2. Configuration of Reflection Suppression Section)

Next, the configuration of the reflection suppression section 12 will be described. The reflection suppression section 12 is a concave-convex structure formed on the surface (herein, both the front and back faces) of the optical film 10. Obviously, the reflection suppression section 12 is not limited to this example, and may be anything having a function of suppressing the reflection of the imaging light.

Specifically, the reflection suppression section 12 includes multiple convexities 12a which are convex in the film-thickness direction of the substrate film 11, and multiple concavities 12b which are concave in the film-thickness direction of the substrate film 11. The convexities 12a and the concavities 12b are arranged periodically on the substrate film 11. In the example of FIG. 7, the convexities 12a and the concavities 12b are arranged in a staggered lattice. Obviously, the convexities 12a and the concavities 12b may also be arranged in a different arrangement pattern. For example, the convexities 12a and the concavities 12b may also be arranged in a square lattice. Additionally, the convexities 12a and the concavities 12b may also be arranged randomly. The shapes of the convexities 12a and the concavities 12b are not particularly limited. The shapes of the convexities 12a and the concavities 12b may also be conical, columnar, or needle-shaped, for example. Note that the shape of the concavities 12b means the shape formed by the inner wall faces of the concavities 12b.

The average cycle of the concavities and convexities of the reflection suppression section 12 is less than or equal to the visible light wavelengths (for example, less than or equal to 830 nm), preferably between 100 nm and 350 nm, and more preferably between 150 nm and 280 nm. Consequently, the reflection suppression section 12 has what is called a moth-eye structure. Herein, if the average cycle is less than 100 nm, there is a possibility that the formation of the reflection suppression section 12 may become difficult, which is not preferable. Also, if the average cycle exceeds 350 nm, there is a possibility that a diffraction phenomenon of visible light may occur, which is not preferable.

The average cycle of the reflection suppression section 12 is the arithmetic mean value of the distance between adjacent convexities 12a and between adjacent concavities 12b (also known as the concavity-convexity pitch). Note that the shape of the reflection suppression section 12 is observable with a scanning electron microscope (SEM), a cross-sectional transmission electron microscope (cross-sectional TEM), or the like, for example. Also, a method for calculating the average cycle is as follows, for example. Namely, multiple pairs of adjacent concavities 12b and pairs of adjacent convexities 12a are picked up, and the distance therebetween is measured. Note that it is sufficient for the distance between the convexities 12a to be the distance between the apices of the convexities 12a. It is sufficient for the distance between the concavities 12b to be the distance between the center points of the concavities 12b. Subsequently, the average cycle may be calculated by taking the arithmetic average of the measured values. Note that, in FIGS. 6 and 7, the reflection suppression section 12 is formed on both faces of the substrate film 11, but it is sufficient to form the reflection suppression section 12 on at least one surface. Furthermore, the height of the convexities 12a of the reflection suppression section 12 may be approximately from 180 nm to 270 nm, and preferably from 200 nm to 250 nm. The height of the convexities 12a is observable by cross-sectional SEM, for example.

The reflection suppression section 12 includes a cured curing resin. The cured curing resin is demanded to at least be transparent. For example, the refractive index of the cured curing resin preferably is approximately the same as that of the substrate film 11. In this case, since internal reflections of the optical film 10 can be suppressed, quality degradation of the captured image can be suppressed more reliably.

The curing resin includes a polymerizable compound and a curing initiator. The polymerizable compound is a resin that is cured by being polymerized by the curing initiator. The curing resin preferably is a hydrophilic resin. In this case, the reflection suppression section 12 can additionally suppress fogging of the optical film 10. In other words, since the reflection suppression section 12 has a concave-convex structure in which the pitch of the concavities and convexities is less than or equal to the visible light wavelengths, a fogging suppression function that is higher than a flat film is included. In other words, the reflection suppression section 12 also functions as a fogging suppression section. However, to further raise the fogging suppression function of the reflection suppression section 12, the curing resin preferably is a hydrophilic resin.

In other words, depending on the use environment of the endoscope device 100, there is a possibility that the humidity inside the endoscope camera drape 200 may rise. For example, there is a possibility that a change in the temperature and humidity environment of the operating room may cause the humidity inside the endoscope camera drape 200 to rise. Also, in surgeries that use water, there is likewise a possibility that the humidity inside the endoscope camera drape 200 may rise. Additionally, in the case in which the humidity inside the endoscope camera drape 200 rises, the surface of the optical film 10 becomes fogged more easily. Additionally, if fogging, condensation, or the like occurs on the surface of the optical film 10, there is a possibility that the quality of the captured image may become degraded. Consequently, a high fogging suppression function is demanded of the optical film 10 in some cases. Consequently, the curing resin preferably is a hydrophilic resin.

From such perspectives, the polymerizable compound preferably is hydrophilic monomers (or alternatively, an oligomer or a prepolymer including these hydrophilic monomers). Examples of hydrophilic monomers include polyoxyalkyl-containing (meth-)acrylate, quaternary ammonium salt-containing (meth-)acrylate, ternary amino group-containing (meth-)acrylate, sulfonic acid group-containing monomers, carboxylic acid group-containing monomers, phosphoric acid group-containing monomers, phosphonic acid group-containing monomers, and the like. Herein, (meth-)acrylate means acrylate or methacrylate. The same applies to (meth-) acryloyl and (meth-)acryl.

Examples of polyoxyalkyl-containing (meth-)acrylate include mono- or polyacrylate, mono- or polymethacrylate, or the like obtained by a reaction between a polyhydric alcohol (a compound containing polyol or polyhydroxy) and a compound selected from the group consisting of acrylic acid, methacrylic acid, and their derivatives. Examples of polyhydric alcohols include dihydric alcohol, trihydric alcohol, tetrahydric or higher alcohol, and the like. Examples of dihydric alcohol include ethylene glycol, diethylene glycol, triethylene glycol, tetraethylene glycol, polyethylene glycol with a number average molecular weight from 300 to 1,000, propylene glycol, dipropylene glycol, 1,3-propanediol, 1,4-butanediol, 1,5-pentanediol, 1,6-hexanediol, neopentyl glycol, 2-ethyl-1,3-hexanediol, 2,2'-thiodiethanol, 1,4-cyclohexanedimethanol, and the like. Examples of trihydric alcohol include trimethylolethane, trimethylolpropane, pentaglycerol, glycerol, 1,2,4-butanetriol, 1,2,6-hexanetriol, and the like. Examples of tetrahydric or higher alcohol include pentaerythritol, diglycerol, dipentaerythritol, and the like.

Examples of polyoxyalkyl-containing (meth-)acrylate include polyethylene glycol (meth-)acrylate, polypropylene glycol (meth-)acrylate, and the like. Examples of polyethylene glycol (meth-)acrylate include methoxy-polyethylene glycol (meth-)acrylate and the like. The molecular weight of the polyethylene glycol unit in the polyethylene glycol (meth-)acrylate is not particularly limited, can be selected appropriately in accordance with the objective, and may be from 300 to 1,000 or the like, for example. As the methoxy-polyethylene glycol (meth-)acrylate, any of various commercial products can also be used.

Among these, polyethylene glycol (meth-)acrylate is preferable, and methoxy-polyethylene glycol (meth-)acrylate is more preferable.

Examples of the quaternary ammonium salt-containing (meth-)acrylate include (meth-)acryloyl oxyethyltrimethyl ammonium chloride, (meth-)acryloyl oxyethyldimethylbenzyl ammonium chloride, (meth-)acryloyl oxyethyldimethylglycidyl ammonium chloride, (meth-)acryloyl oxyethyltrimethyl ammonium methyl sulfate, (meth-)acryloyl oxydimethylethyl ammonium ethyl sulfate, (meth-)acryloyl oxyethyltrimethyl ammonium-p-toluene sulfonate, (meth-)acryl amidopropyltrimethyl ammonium chloride, (meth-)acryl amidopropyldimethylbenzyl ammonium chloride, (meth-)acryl amidopropyldimethylglycidyl ammonium chloride, (meth-)acryl amidopropyltrimethyl ammonium methyl sulfate, (meth-)acryl amidopropyldimethylethyl ammonium ethyl sulfate, (meth-)acryl amidopropyltrimethyl ammonium-p-toluene sulfonate, and the like.

Examples of ternary amino group-containing (meth-)acrylate include N,N-dimethylaminoethyl (meth-)acrylate, N,N-dimethylaminopropyl (meth-)acrylamide, diethylaminopropyl (meth-)acrylimide, 1,2,2,6,6-pentamethylpiperidyl (meth-) acrylate, 2,2,6,6-tetramethylpiperidyl (meth-)acrylate, and the like.

Examples of sulfonic acid group-containing monomers include vinyl sulfonic acid, allyl sulfonic acid, vinyl toluene sulfonic acid, styrene sulfonic acid, sulfonic acid group-containing (meth-)acrylate, and the like. Examples of sulfonic acid group-containing (meth-)acrylate include (meth-) acrylic acid sulfoethyl, (meth-) acrylic acid sulfopropyl, 2-acrylamide-2-methylpropane sulfonic acid, branched sulfonic acid-denatured polyethylene glycol mono-(meth-) acrylate, and the like. These may also form salts. Examples of the salts include sodium salts, potassium salts, ammonium salts, and the like.

Examples of carboxylic acid group-containing monomers include acrylic acid, methacrylic acid, and the like. Examples of phosphoric acid group-containing monomers include (meth-)acrylate including phosphate. The hydrophilic monomers preferably are monofunctional hydrophilic monomers. The molecular weight of the hydrophilic monomers is not particularly limited, and can be selected appropriately in accordance with the objective, but preferably is 200 or more. The hydrophilic monomer content occupying the curing resin is not particularly limited, and can be selected appropriately in accordance with the objective, but preferably is from 15 wt % to 99.9 wt % with respect to the total mass of the curing resin, more preferably from 20 wt % to 90 wt %, and particularly preferably from 25 wt % to 50 wt %.

Instead of hydrophilic monomers, it is possible to use a polymer into which is introduced a photosensitive group including one or more selected from among an azide group, a phenyl azide group, a quinone azide group, a stilbene group, a chalcone group, a diazonium group, a cinnamic acid group, an acrylic acid group, and the like. Examples of the polymer include a polyvinyl alcohol type, a polyvinyl butyral type, a polyvinyl pyrrolidone type, a polyacrylamide type, polyvinyl acetate-type polymers, polyoxyalkylene-type polymers, and the like.

Note that the curing resin is not limited to the above examples. For example, the curing resin may be any kind of resin used in the manufacturing of a moth-eye structure. Examples of curing resins other than the above include a polymerizable epoxy compound and the like. A polymerizable epoxy compound is a monomer, oligomer, or prepolymer having one or two or more epoxy groups in the molecule. Examples of polymerizable epoxy compounds include various bisphenol epoxy resins (such as bisphenol A and F), novolac epoxy resin, various modified epoxy resins such as rubber and urethane, naphthalene epoxy resin, biphenyl epoxy resin, phenol novolac epoxy resin, stilbene epoxy resin, triphenol methane epoxy resin, dicyclopentadiene epoxy resin, triphenyl methane epoxy resin, prepolymers of the above, and the like.

The curing initiator is a material that cures the curing resin. Examples of the curing initiator include heat-curing initiators, light-curing initiators, and the like. The curing initiator may also be one that cures by some kind of energy beam (for example, an electron beam) other than heat or light, or the like. In the case in which the curing initiator is a heat-curing initiator, the curing resin is a thermosetting resin, whereas in the case in which the curing initiator is a light-curing initiator, the curing resin is a light-curing resin.

Herein, the curing initiator preferably is an ultraviolet light-curing initiator. Consequently, the curing resin preferably is an ultraviolet light-curing resin. An ultraviolet light-curing initiator is a type of light-curing initiator. Examples of ultraviolet light-curing initiators include 2,2-dimethoxy-1,2-diphenylethane-1-one, 1-hydroxy-cyclohexyl phenyl ketone, 2-hydroxy-2-methyl-1-phenyl propane-1-one, and the like.

Various types of additives may also be added to the curing resin in accordance with the characteristics demanded of the optical film 10 and the like. Examples of such additives include inorganic fillers, organic fillers, leveling agents, surface conditioners, antifoaming agents, and the like. Note that examples of types of inorganic fillers include metallic oxide particles such as $SiO_2$, $TiO_2$, $ZrO_2$, $SnO_2$, and $Al_2O_3$.

Figure 6:
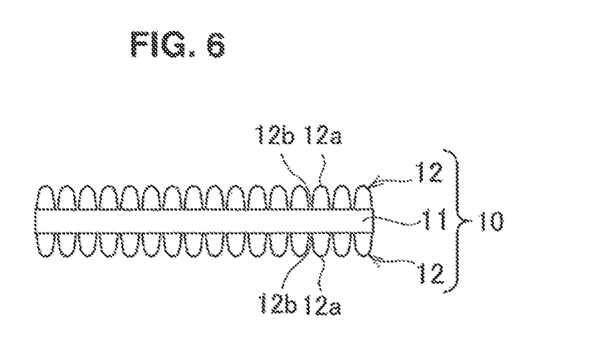
FIG. 6 is a sectional view illustrating an example of an optical film.
Figure 7:
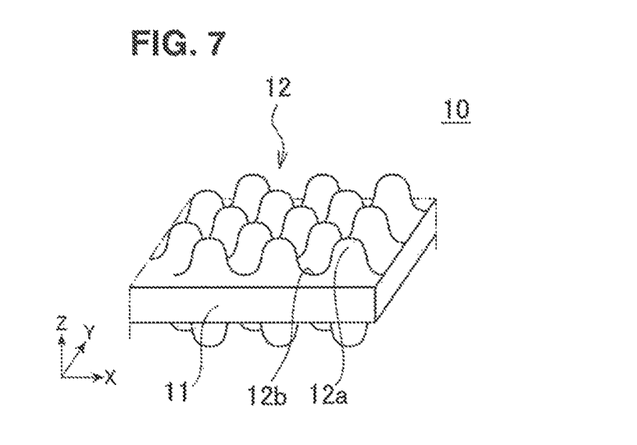
FIG. 7 is a perspective view illustrating an example of an optical film.

In FIGS. 6 and 7, the reflection suppression section 12 is formed on both faces of the substrate film 11. These materials and characteristics of the reflection suppression section 12 may be the same or different. In other words, these materials and characteristics of the reflection suppression section 12 may be decided in accordance with the characteristics demanded of the optical film 10 and the like. For example, of both the front and back faces of the substrate film 11, the reflection suppression section 12 formed on the face opposite to the interior of the endoscope camera drape 200 may include a hydrophilic resin. This is because, as described above, there is a possibility that the humidity inside the endoscope camera drape 200 may rise.

In this way, since the optical film 10 according to the present embodiment is provided with the reflection suppression section 12, an excellent reflection suppression function can be imparted to the optical film 10. Specifically, when the imaging light is incident on the surface of the optical film 10, the refractive index varies continuously in the advancement direction of the imaging light. Note that, in the case in which the refractive index varies suddenly in any part in the advancement direction of the imaging light, that part becomes an optical interface. Additionally, the imaging light is reflected at that part. In the present embodiment, since the reflection suppression section 12 is formed on the surface of the optical film 10, the refractive index varies continuously at that part. In other words, the surface of the optical film 10 is unlikely to become an optical interface. For this reason, the optical film 10 is unlikely to reflect the imaging light.

Note that, in the case in which the irradiating light is taken to be visible light, the spectral reflectance of the visible light preferably is from 0.1% to 1.8%. By giving the reflection suppression section 12 the configuration described above, the spectral reflectance of the visible light can be kept from 0.1% to 1.8%. Also, the total luminous transmittance preferably is 90% or greater, and more preferably is 95% or greater. Herein, the reflection suppression section 12 may be formed integrally with the substrate film 11. In this case, the substrate film 11 includes the material included in the reflection suppression section 12, that is, the curing resin.

<6. Optical Film Production Method>

The optical film production method is not particularly limited, and insofar as the method is able to form the reflection suppression section 12 described above on the substrate film 11, the method is not particularly limited. Schematically, the optical film production method is divided into a first step of preparing the substrate film 11, and a second step of forming the reflection suppression section 12 on the substrate film 11. Examples of the second step include a step of preparing a master, on the surface of which is formed a concave-convex structure having the inverse shape of the concave-convex structure of the reflection suppression section 12, transferring the concave-convex structure of the master onto the substrate film 11, and the like.

Herein, the method for preparing the master is not particularly limited. For example, the master may be manufactured by thermal lithography and dry etching. With this method, schematically, first a resist layer is formed on the surface of a master substrate. Subsequently, the resist layer is irradiated with laser light and later developed, thereby forming a concave-convex structure on the resist layer. Next, by dry etching with the resist layer acting as a mask, a concave-convex structure is formed on the surface of the master substrate. With this arrangement, the master is manufactured. Note that the concave-convex structure of the resist layer may also be transferred onto the substrate film.

Additionally, the master may also be manufactured by an anodic oxidation method. A master production method by an anodic oxidation method is disclosed in, for example, JP 2013-142802A. With this method, by performing an anodic oxidation process on a master substrate, a concave-convex structure is formed on the surface of the master substrate. With this arrangement, the master is manufactured. The pitch of the concave-convex structure is controllable by the formation voltage during the anodic oxidation process. Note that, in JP 2013-142802A, an anodic oxidation process is performed in two stages with mutually different formation voltages, but the present embodiment is not limited to this method.

Also, the master may be manufactured by mechanically cutting a master substrate. A method for mechanically cutting a master substrate is disclosed in, for example, JP 2004-223836A. With this method, by using a tool such as a diamond-point tool to cut the surface of a master substrate, a concave-convex structure is formed on the surface of the master substrate. Note that, in the method disclosed in JP 2004-223836A, a concave-convex structure is formed on the surface of a master substrate having a cylindrical shape by forming helical grooves that intersect each other on the surface of the master substrate, but the present embodiment is not limited to this method.

The shape of the master is not particularly limited, and may be a cylindrical shape or a columnar shape. In this case, the optical film can be manufactured continuously by roll-to-roll.

Also, the method for transferring the concave-convex structure of the master onto the substrate film 11 is not particularly limited. For example, an uncured curing resin layer is formed on the substrate film 11, and the concave-convex structure of the master is transferred onto the curing resin layer. Next, it is sufficient to cure the curing resin layer. In addition, the concave-convex structure of the master may also be transferred directly onto the substrate film 11. In this case, the substrate film 11 is formed by a thermoplastic resin, for example. Subsequently, the substrate film 11 is softened by being heated, and the concave-convex structure of the master is transferred onto the substrate film 11.

Additionally, the second step may also be performed without using a master. In this case, for example, first a resist layer is formed on the substrate film 11. Next, by exposing and developing the resist layer, the reflection suppression section 12 is formed on the substrate film 11.

Working Example

<1. Manufacture of Connecting Member>

By the steps below, connecting members according to working examples 1 to 3, a comparative example, and a reference example were manufactured. In working example 1, the endoscope camera engagement section, the endoscope engagement section, and the blocking section (that is, of the connecting member, the part other than the optical film) having the structure illustrated in FIG. 5 were manufactured by vacuum forming. The material of the endoscope camera engagement section, the endoscope engagement section, and the blocking section was taken to be polyethylene terephthalate (PET). On the other hand, the optical film was manufactured by the following steps. Namely, a polycarbonate film (Panlite, made by Teijin Limited) was prepared as the substrate film. Additionally, a master having the inverse shape of the concave-convex structure of the reflection suppression section was prepared. Herein, the arrangement pattern of the concave-convex structure of the reflection suppression section was taken to be a staggered lattice. Also, the concavity-convexity pitch of the reflection suppression section was taken to be from 230 nm to 270 nm. Also, the height of the convexities was taken to be from 200 nm to 250 nm. Subsequently, this master was used to form the reflection suppression section on both the front and back faces of the substrate film.

Herein, an ultraviolet light-curing acrylic resin composition made by Toagosei Co., Ltd. was used as the curing resin. With this arrangement, the optical film was manufactured. Next, double-sided tape (LUCIACS 25 microns, made by Azuma Denko Corporation) was used to bond the optical film to the front and back faces of the blocking section. By the above steps, the connecting member according to working example 1 was created.

In working example 2, besides bonding the optical film only to the surface of the blocking section on the endoscope side, by performing steps similar to those of working example 1, the connecting member according to working example 2 was manufactured. In working example 3, besides bonding the optical film only to the surface of the blocking section on the endoscope camera side, by performing steps similar to those of working example 1, the connecting member according to working example 3 was manufactured. In the comparative example, other than bonding a PET film on which the reflection suppression section is not formed instead of the optical film onto both faces of the blocking section, by performing steps similar to those of working example 1, the connecting member according to the comparative example was manufactured. In the reference example, the connecting member was taken to be one in which the optical film is removed from the connecting member illustrated in FIG. 1 (in other words, one in which the location where the optical film exists has become a cavity).

<2. Evaluation of Optical Characteristics>

Next, the optical characteristics of the connecting members according to working examples 1 to 3 and the comparative example were evaluated. Specifically, the total luminous transmittance (%) and the haze value (%) of the central part of the connecting member (that is, the part where the optical film or the PET film is attached) were evaluated. Herein, the total luminous transmittance was measured in compliance with JIS K7361, and the haze value was measured in compliance with JIS K7136. Additionally, regarding the total luminous transmittance, the case of a total luminous transmittance (equal to or greater than 95%) was evaluated as VG (Very Good), the case of a total luminous transmittance (equal to or greater than 90%, less than 95%) was evaluated as G (Good), and the case of a total luminous transmittance (less than 90%) was evaluated as B (Bad). Also, regarding the haze value, the case of a haze value (less than or equal to 1.0%) was evaluated as VG (Very Good), the case of a haze value (greater than 1.0%, less than or equal to 1.2%) was evaluated as G (Good), and the case of a haze value (greater than 1.2%) was evaluated as B (Bad).

As a result, in working example 1, both the total luminous transmittance and the haze value were VG while, in working examples 2 and 3, both the total luminous transmittance and the haze value were G On the other hand, in the comparative example, both the total luminous transmittance and the haze value were B.

<3. Image Evaluation>

Next, the appearances of images when applying the connecting members according to working examples 1 to 3 and the comparative example to an endoscope device were evaluated. Specifically, an endoscope (Perecision IE Laparoscope made by Stryker), an endoscope camera (High Definition 1488HD made by Stryker), and the connecting members according to working examples 1 to 3, the comparative example, and the reference example were used to assemble endoscope devices. The endoscope camera drape was omitted. Next, irradiating light was radiated from the tip of the endoscope onto a sample drawing drawn on paper, and imaging light was made to be incident on the endoscope camera. Additionally, the image captured by the endoscope camera was displayed on a display device. Subsequently, the quality of the image displayed on the display device was evaluated visually. Specifically, the images obtained by working examples 1 to 3 and the comparative example were evaluated, using the image obtained by the reference example as a base of reference. As a result, in working examples 1 to 3, images of a quality commensurate with the image of the reference example were obtained, whereas the image obtained by the comparative example was of much lower quality than that of the image of the reference example. Particularly, the image of the comparative example was greatly blurred as compared to the image of the reference example. Also, comparing working examples 1 to 3, working example 1 exhibited the least amount of blur. Such blur is thought to be affected greatly by the total luminous transmittance and the haze value described above. According to the above results, it is apparent that the connecting members according to working examples 1 to 3 are extremely favorable for an endoscope device.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 10 optical film
11 substrate film
12 reflection suppression section
100 endoscope device
110 endoscope
111 base section
112 insertion section
120 light radiation cable
130 endoscope camera
135 connecting member engagement section
140 endoscope camera cable
200 endoscope camera drape
210 drape section
220 connecting member
222 endoscope camera engagement section
225 endoscope engagement section

The invention claimed is:

1. An optical film provided on an endoscope camera drape including a drape section that covers a circumferential face of an endoscope camera, and a connecting member which is provided on a front end of the drape section and connects an endoscope and the endoscope camera, the optical film being provided on the connecting member, further comprising:
a reflection suppression section configured to suppress a reflection of incident light incident on the endoscope camera from the endoscope,
wherein the reflection suppression section is formed on both faces of the optical film,
wherein the reflection suppression section is a concave-convex structure formed on a surface of the optical film,
wherein a pitch of concavities and convexities included in the concave-convex structure of the reflection suppression section is less than or equal to a visible light wavelength,
wherein a surface of the optical film facing the endoscope is covered by a protective film,
wherein a concave-convex structure is also provided on the protective film, and
wherein a pitch of concavities and convexities of the concave-convex structure of the protective film is smaller than the pitch of the concavities and convexities of the concave-convex structure of the reflection suppression section.

2. The optical film according to claim 1, wherein a spectral reflectance of visible light from the optical film is from 0.1% to 1.8%.

3. The optical film according to claim 1, wherein
the reflection suppression section suppresses fogging of the optical film.

4. The optical film according to claim 3, wherein
the reflection suppression section includes a hydrophilic resin.

5. The optical film according to claim 1, comprising:
a polycarbonate resin.

6. The optical film according to claim 5, wherein
the optical film includes a substrate film, and the reflection suppression section formed on a surface of the substrate film, and
the substrate film includes the polycarbonate resin.

7. A connecting member provided on a front end of a drape section that covers a circumferential face of an endoscope camera, and connects an endoscope and the endoscope camera, further comprising:
an optical film comprising a reflection suppression section configured to suppress a reflection of incident light incident on the endoscope camera from the endoscope,
wherein the reflection suppression section is formed on both faces of the optical film,
wherein the reflection suppression section is a concave-convex structure formed on a surface of the optical film,
wherein a pitch of concavities and convexities included in the concave-convex structure of the reflection suppression section is less than or equal to a visible light wavelength,
wherein a surface of the optical film facing the endoscope is covered by a protective film,
wherein a concave-convex structure is also provided on the protective film, and
wherein a pitch of concavities and convexities of the concave-convex structure of the protective film is smaller than the pitch of the concavities and convexities of the concave-convex structure of the reflection suppression section.

8. The connecting member according to claim 7, wherein the protective film is a molded item having a shape conforming to a surface shape of the connecting member.

9. An endoscope device comprising: the connecting member according to claim 7.

10. A medical system comprising:
the endoscope device according to claim 9.

11. An optical film production method for producing the optical film according to claim 1, the optical film production method comprising:
a first step of preparing a substrate film;
a second step of forming, on a surface of the substrate film, the reflection suppression section that suppresses a reflection of incident light incident on the endoscope camera from the endoscope, and
providing the optical film on the connecting member in the endoscope camera drape including the drape section that covers the circumferential face of the endoscope camera, and the connecting member which is provided on the front end of the drape section and connects the endoscope and the endoscope camera.

12. The optical film production method according to claim 11, wherein the reflection suppression section includes a hydrophilic resin.

13. The optical film production method according to claim 11, wherein
the substrate film includes a polycarbonate resin.

14. A connecting member production method of producing a connecting member provided on a front end of a drape section that covers a circumferential face of an endoscope camera, the connecting member connecting an endoscope and the endoscope camera, the connecting member production method comprising:
manufacturing the connecting member using the optical film according to claim 1.

15. The connecting member production method according to claim 14, wherein the connecting member is manufactured by monolithically molding the optical film in a shape of the connecting member.

* * * * *